United States Patent
Malik et al.

(10) Patent No.: US 11,865,067 B2
(45) Date of Patent: Jan. 9, 2024

(54) TRANSCUTANEOUS ELECTRICAL STIMULATION AND LIGHT STIMULATION DEVICES FOR TREATING HYPERTENSION USING ELECTRICAL OR LIGHT ENERGY APPLIED TO PREDEFINED ACUPUNCTURE POINTS

(71) Applicant: Shaista Malik, Tustin, CA (US)

(72) Inventors: Shaista Malik, Tustin, CA (US); Stephanie C Tjen-A-Looi, Lake Forest, CA (US); Lifang Xie, Irvine, CA (US); Liang-Wu Fu, Irvine, CA (US); Peng Li, Irvine, CA (US)

( * ) Notice: Subject to any disclaimer, the term of this patent is extended or adjusted under 35 U.S.C. 154(b) by 0 days.

(21) Appl. No.: 17/580,317

(22) Filed: Jan. 20, 2022

(65) Prior Publication Data
US 2022/0211577 A1    Jul. 7, 2022

Related U.S. Application Data

(63) Continuation of application No. 16/391,708, filed on Apr. 23, 2019, now Pat. No. 11,259,989.
(Continued)

(51) Int. Cl.
*A61N 1/36* (2006.01)
*A61N 1/04* (2006.01)
(Continued)

(52) U.S. Cl.
CPC ........... *A61H 39/002* (2013.01); *A61H 39/04* (2013.01); *A61H 39/08* (2013.01); *A61N 1/0408* (2013.01);
(Continued)

(58) Field of Classification Search
CPC ...... A61H 39/002; A61H 39/04; A61H 39/08; A61H 2039/005; A61H 2201/0153; A61H 2201/0157; A61H 2201/1207; A61H 2201/1654; A61H 2201/5023; A61H 39/007; A61N 1/0408; A61N 1/36014; A61N 1/0472; A61N 1/0456;
(Continued)

(56) References Cited

U.S. PATENT DOCUMENTS 8,805,512 B1    8/2014 Greiner
8,965,511 B2    2/2015 Greiner
(Continued)

OTHER PUBLICATIONS

Longhurst et al., "Evidence-based blood pressure reducing actions of Electroacupuncture: mechanisms and clinical application", Acta Physiologica Sinica, Oct. 25, 2017, 69(5): 587-597; DOI: 10.13294/j.aps.2017.0035; http://www.actaps.com.cn.
(Continued)

*Primary Examiner* — Carl H Layno
*Assistant Examiner* — Anh-Khoa N Dinh
(74) *Attorney, Agent, or Firm* — Novel IP

(57) ABSTRACT

Energy stimulated acupuncture, directed to a novel set of acupoints, is implemented to treat hypertension. Methods and systems apply electrical stimulation, or other forms of energy, to specific acupuncture points, using devices such as transcutaneous electrical stimulation electroacupuncture devices, laser acupuncture devices or ultrasound acupuncture devices, to treat hypertension, particularly in middle-aged women.

17 Claims, 4 Drawing Sheets

Related U.S. Application Data

(60) Provisional application No. 62/661,190, filed on Apr. 23, 2018.

(51) Int. Cl.
    *A61H 39/08*     (2006.01)
    *A61H 39/04*     (2006.01)
    *A61H 39/00*     (2006.01)
    *G16H 20/30*     (2018.01)

(52) U.S. Cl.
    CPC ........ *A61N 1/36014* (2013.01); *A61N 1/0472* (2013.01); *G16H 20/30* (2018.01)

(58) Field of Classification Search
    CPC .... A61N 1/36034; G16H 20/30; G16H 20/40; G16H 40/63
    See application file for complete search history.

(56) References Cited

U.S. PATENT DOCUMENTS

| | | | |
|---|---|---|---|
| 9,327,134 B2 | 5/2016 | Greiner | |
| 2006/0041283 A1* | 2/2006 | Gelfand | A61N 1/36114 607/44 |
| 2007/0098814 A1 | 5/2007 | Xu | |
| 2011/0301671 A1* | 12/2011 | Lytle | A61N 5/0613 726/5 |
| 2014/0039238 A1* | 2/2014 | Min | A61B 5/4818 607/18 |
| 2014/0214115 A1* | 7/2014 | Greiner | A61N 1/37205 607/44 |
| 2016/0128933 A1* | 5/2016 | Shang | A61K 31/045 514/64 |

OTHER PUBLICATIONS

Li et al., "Long-Lasting Reduction of Blood Pressure by Electroacupuncture in Patients with Hypertension: Randomized Controlled Trial", Medical Acupuncture, vol. 27, No. 4, 2015; DOI 10.1089/acu.2015.1106.

Guo et al., "Role of TRPV1 in acupuncture modulation of reflex excitatory cardiovascular responses", Am J Physiol Regul Integr Comp Physiol, 314: R655-R666, 2018. First Published Jan. 3, 2018; doi:10.1152/ajpregu.00405.2017.

\* cited by examiner

TRANSCUTANEOUS ELECTRICAL STIMULATION AND LIGHT STIMULATION DEVICES FOR TREATING HYPERTENSION USING ELECTRICAL OR LIGHT ENERGY APPLIED TO PREDEFINED ACUPUNCTURE POINTS

CROSS-REFERENCE

The present application is a continuation application of U.S. patent application Ser. No. 16/391,708, entitled "Methods and Systems for Treating Hypertension Using Energy-Stimulated Acupuncture Applied to Predefined Acupuncture Points", now U.S. Pat. No. 11,259,989 B2, and filed on Apr. 23, 2019, which relies on, for priority, U.S. Patent Provisional Application No. 62/661,190,10 entitled "Methods and Systems for Treating Hypertension Using Electroacupuncture Applied to Predefined Acupuncture Points" and filed on Apr. 23, 2018, both of which are hereby incorporated by reference in their entirety.

FIELD

The present specification is directed toward the use of energy-stimulated acupuncture to treat hypertension. More specifically, the present specification is directed toward the application of energy stimulation to specific acupuncture points, using devices such as transcutaneous electrical stimulation electroacupuncture devices, laser acupuncture devices or ultrasound acupuncture devices, to treat hypertension.

BACKGROUND

Aging increases sympathetic activity leading to hypertension and increased cardiovascular events such as stroke. Aging also is associated with a progressive decline in female sex hormone production such as estradiol and may predispose women to hypertension. Declining estradiol potentiates menopausal hypertension while experimental studies show reduction of sympathetic activity in the presence of estradiol. A prospective population study shows that a reduction in estradiol potentiates postmenopausal hypertension suggesting that estradiol is an important consideration in the management of elevated blood pressure. Over half of the women on antihypertensive medications remain hypertensive.

Prior studies have shown that applying electroacupuncture (EA) at predefined acupuncture points, P5-6 and St36-37, reduces blood pressure and sympathetic activity in a group of male and female patients with mild to moderate hypertension (HTN). Over an eight week treatment period, patients experienced a blood pressure reduction by week four using EA treatment for 30 minutes once a week. After 8 weeks of EA sessions, the reduction in blood pressure was sustained for at least a month. However, a majority (64%) of middle-aged women with hypertension were not responsive to this treatment.

For example, U.S. Pat. No. 8,805,512, assigned to Valencia Technologies Corporation, describes "[a]n implantable electroacupuncture device (LEAD)" that "treats hypertension through application of stimulation pulses applied at least one of acupoints PC5, PC6, ST36 or ST37". Further, U.S. Pat. No. 8,965,511, also assigned to Valencia Technologies Corporation, describes "[a]n implantable electroacupuncture device (LEAD)" that "treats hypertension through application of stimulation pulses applied at least one of acupoints PC5, PC6, LI4, ST36, ST37, LI11, LR3, and GB34". And finally, U.S. Pat. No. 9,327,134, also assigned to Valencia Technologies Corporation, describes "[a]n implantable electroacupuncture device (LEAD)" that "treats a medical condition of a patient through application of electroacupuncture stimulation pulses applied at a target tissue location, such as an acupoint". These approaches have significant disadvantages, however. First, they require the electrodes to be implanted. Second, the efficacy for treating hypertension, particularly in middle age women, is likely to be insufficient.

What is needed, therefore, is a well-defined energy stimulation, particularly EA, treatment for hypertension that may be independently and readily implemented by patients independent of healthcare practitioners. What is also needed is an EA treatment for hypertension that does not require electrodes to be implanted into the patient's skin. Further, what is needed is an EA treatment that more effectively treats hypertension in women, particularly by influencing the hypothalamic-ovarian axis.

SUMMARY

The following embodiments and aspects thereof are described and illustrated in conjunction with systems, tools and methods, which are meant to be exemplary and illustrative, and not limiting in scope. The present application discloses numerous embodiments.

The present specification discloses a method for treating hypertension in a patient comprising: applying a plurality of applicator elements to a plurality of acupoints, wherein the plurality of applicator elements is positioned in physical contact with each of the plurality of acupoints and wherein the plurality of acupoints comprise P6, LI4, St36, Sp6, CV3, CV4, LR3, and KI3; and using a stimulation device coupled with each of the plurality of applicator elements, applying energy to each of the plurality of applicator elements for a stimulation session.

Optionally, the plurality of applicator elements comprise at least one of a needle, an electrode, an electrode pads or an electrode contact.

Optionally, the energy applied is electrical current and wherein the stimulation session is defined by a pulse amplitude in a range of 0.5 mA to 8 mA.

Optionally, the pulse amplitude is in a range of 1 mA to 2 mA.

Optionally, the energy applied is electrical current and wherein the stimulation session is defined by a pulse frequency in a range of 0.2 Hz to 10 Hz.

Optionally, the pulse frequency is in a range of 2 Hz to 5 Hz.

Optionally, the energy applied is electrical current and wherein the stimulation session is defined by a time period in a range of one minute to three hours.

Optionally, the stimulation session is applied at least once per week.

Optionally, the stimulation session is applied no more than five times per week.

Optionally, in the stimulation session, the energy is applied to each of the plurality of applicator elements concurrently.

Optionally, in the stimulation session, the energy is not applied to each of the plurality of applicator elements concurrently.

The present specification also discloses a method for treating hypertension in a patient comprising: directing a plurality of laser energy applicator elements to a plurality of acupoints, wherein the plurality of laser energy applicator elements is directed toward each of the plurality of acupoints and wherein the plurality of acupoints comprise P6, LI4, St36, Sp6, CV3, CV4, LR3, and KI3; and using a laser device coupled with each of the plurality of laser energy applicator elements, applying laser energy to each of the plurality of laser energy applicator elements for a stimulation session.

Optionally, the stimulation session is defined by a time period in a range of one minute to three hours.

Optionally, the stimulation session is applied at least once per week.

Optionally, the stimulation session is applied no more than five times per week.

Optionally, in the stimulation session, the laser energy is applied to each of the plurality of laser energy applicator elements concurrently.

Optionally, in the stimulation session, the laser energy is not applied to each of the plurality of laser energy applicator elements concurrently.

The present specification also discloses a method for treating hypertension in a patient comprising: directing a plurality of electrical energy applicator elements to a plurality of acupoints, wherein the plurality of electrical energy applicator elements is directed toward each of the plurality of acupoints and wherein the plurality of acupoints comprise P6, LI4, St36, Sp6, CV3, CV4, LR3, and KI3; and using an electrical stimulation device coupled with each of the plurality of electrical energy applicator elements, applying electrical energy to each of the plurality of electrical energy applicator elements for a stimulation session.

Optionally, the stimulation session is defined by a time period in a range of 20 seconds to three hours.

Optionally, the stimulation session is applied at least once per week.

Optionally, the stimulation session is applied no more than five times per week.

Optionally, in the stimulation session, the electrical energy is applied to each of the plurality of electrical energy applicator elements concurrently.

Optionally, in the stimulation session, the electrical energy is not applied to each of the plurality of electrical energy applicator elements concurrently.

The aforementioned and other embodiments of the present shall be described in greater depth in the drawings and detailed description provided below.

BRIEF DESCRIPTION OF THE DRAWINGS

These and other features and advantages of the present specification will be further appreciated, as they become better understood by reference to the following detailed description when considered in connection with the accompanying drawings.

DETAILED DESCRIPTION

Figure 1A:
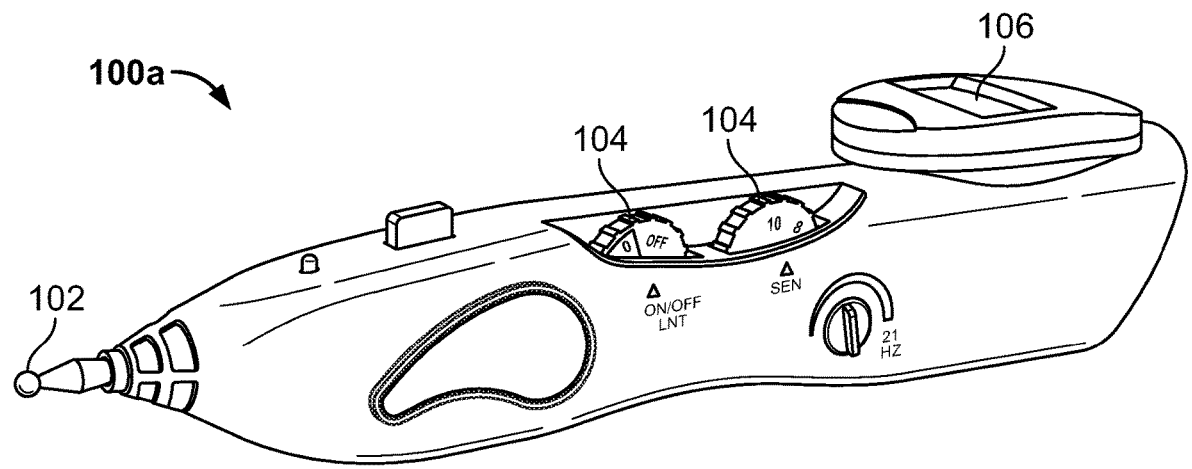
FIG. 1A illustrates an exemplary electro-acupuncture device, in accordance with an embodiment of the present specification.

The present specification is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

In the description and claims of the application, each of the words "comprise" "include" and "have", and forms thereof, are not necessarily limited to members in a list with which the words may be associated. It should be noted herein that any feature or component described in association with a specific embodiment may be used and implemented with any other embodiment unless clearly indicated otherwise.

The term "energy stimulated acupuncture" refers to various acupuncture modalities delivered by a particular energy source including, but not limited to, electroacupuncture, laser acupuncture, and ultrasound acupuncture.

The term "acupuncture points" or "acupoints" refers to a particular anatomical location on the human body and may be more specifically referred to using alphanumeric nomenclature or the English version of Chinese language terms, such as Jiangshi (P5), Neiguan (P6), Zusanli (St36), Shangjuxu (St37), Hegu (LI4), Sanyinjiao (Sp6), Zhongji (CV3), Guanyuan (CV4), Taichong (LI3), and Taixi (KI3, Kid-3, or Kd3).

The novel therapies disclosed herein target, at least in part, perimenopausal hypertension by targeting both a patient's endocrine system and sympathetic tone. The endocrine-sympathoinhibitory EA treatments decrease blood pressure in middle-aged perimenopausal females with mild to moderate hypertension.

Energy Stimulated Acupuncture Devices

The acupuncture therapy of the present specification is directed towards applying energy to one or more of a plurality of specific acupoints in order to stimulate the one or more acupoints and consequently treat one or more ailments. In embodiments, the applied energy may be in the form of pulsating electrical current, laser or ultrasound. The energy is delivered, to the acupoints, in a programmed fashion through applicator elements such as, but not limited to, needles, electrodes, energy emitters, and conductive wires, pads or contacts.

In embodiments, a stimulator device serves as a source of energy and also as a means of controlling and modulating the energy delivered to a patient at the acupoints. In various embodiments, the stimulator device has a housing comprising one or more processors capable of executing programmatic instructions or code, one or more non-transitory memory capable of storing processor executable code and a plurality of maneuverable buttons, switches, dials and/or icons on a touch-sensitive screen to enable an operator to interact with the device and modulate the energy delivered to the patient. In some embodiments, the stimulator device is configured as a battery operated hand-held portable device. The stimulator device is connected, such as by conductive wires or cables, to one or more applicator elements.

In some embodiments, the stimulator device is configured to function as an electro-acupuncture device that serves as a source of electrical energy delivered to the patient at the one or more acupoints. In one embodiment, the associated applicator elements are disposable or re-usable sterile stainless steel needles that are connected to the stimulator device using wires and cables. In an embodiment, the stainless steel needles are inserted bilaterally into one or more acupoints for delivery of electrical energy.

In some embodiments, the stimulator device is configured as a Transcutaneous Electrical Stimulation Device (TENS) that is used to deliver stimulation therapy through one or more surface electrodes, pads or contacts positioned at the acupoints.

FIG. 1A illustrates an exemplary electro-acupuncture device 100a, in accordance with an embodiment of the present specification. Device 100a is configured to provide electrical stimulation at one or more acupoints by attaching its tip 102 through disposable or re-usable sterile stainless steel needles. Buttons and/or knobs 104 are provided to control the power to operate the device, and adjust stimulation parameters such as pulse amplitude, pulse frequency, and pulse phase, of the electrical energy used to perform the acupuncture. A display 106 is provided to enable users to view the settings.

Figure 1B:
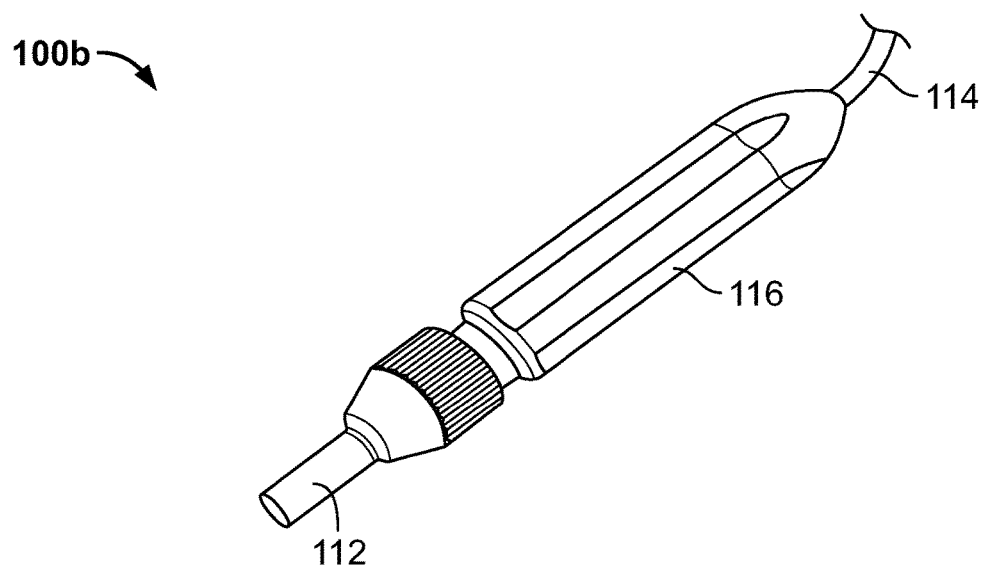
FIG. 1B illustrates an exemplary laser-acupuncture device, in accordance with an embodiment of the present specification.

In some embodiments, the stimulator device is connected, by a radio interface, with a laser unit to deliver laser energy to the patient at the acupoints as part of a laser acupuncture treatment. Light particles (photons) with high excitation density are conducted through fine optical fibers. The fibers do not puncture the skin, but are placed on the therapy points, radiating with high precision into the tissue which requires treatment. FIG. 1B illustrates an exemplary laser-acupuncture device 100b, in accordance with an embodiment of the present specification. Device 100b is configured to provide laser stimulation at one or more acupoints by placing a laser-pointing tip 112 of device 100b on the acupoints and radiating those points with laser. Laser light particles are conducted through fine optical fibers that may be powered by an electrical source connected to device 100b through a wire 114. A housing 116 houses the electrical and optical components and provides a grip to the user to manage and control operation of device 100b.

In one embodiment, the device 100b comprises a laser acupuncture probe operating at a 1) wavelength in a range of 700 to 900 nm, preferably 750 to 850 nm, and more preferably at 808 nm and 2) a power level in a range of 100 to 400 mW, preferably 200 mW. In one embodiment, the device 100b comprises a laser acupuncture probe operating at a 1) a maximum power output is in a range of 50 to 500 mW, more preferably 150 mW, 2) in a continuous wave mode and 3) at a power density of 0.3 to 0.5 W/cm$^2$, preferably 0.417 W/cm$^2$. In one embodiment, the device 100b will be activated and applied to the one or more acupoints, each for a time period in a range of 2 to 30 seconds, or any increment therein, and, more preferably in a range of 10 seconds. In one embodiment, the device 100b will be activated and applied to the one or more acupoints, such that an energy density in a range of 2 to 6 J/cm$^2$, and preferably an energy density of 4 J/cm$^2$, at each point. In another embodiment, the device 100b is activated at each of the one or more acupoints 1) at a wavelength in a range of 700 to 1000 nm, preferably in a range of 800 to 910 nm, preferably at 904 nm, 2) with a power density in a range of 5 to 20 mW/cm$^2$, preferably 10 mW/cm$^2$, 3) with an output power in a range of 2 to 6 mW, preferably 4 mW, 4) with a spot size in a range of 0.2 cm$^2$ to 0.6 cm$^2$, preferably 0.4 cm$^2$ spot size, 5) at an energy dose per session in a range of 0.2 to 0.7 Joules dose per session, preferably 0.48 Joules dose per session, and/or 6) a treatment time in a range of 5 seconds to 240 seconds per acupoint.

In some embodiments, the stimulator device is connected with a sound-head applicator to deliver focused ultrasound energy to the patient at the acupoints as part of an ultrasound acupuncture treatment. The sound-head applicator is put in direct contact with the patient's skin. Ultrasound gel is used on all surfaces of the head in order to reduce friction and assist in the transmission of the ultrasonic waves.

While the preferred treatment method of the present specification is described with reference to electro-acupuncture therapy to deliver electrical energy to specific acupoints, it should be appreciated that the treatment method is equally applicable to delivering other forms of stimulation energy, such as, but not limited to laser and ultrasound.

Acupoints

Figure 1C:
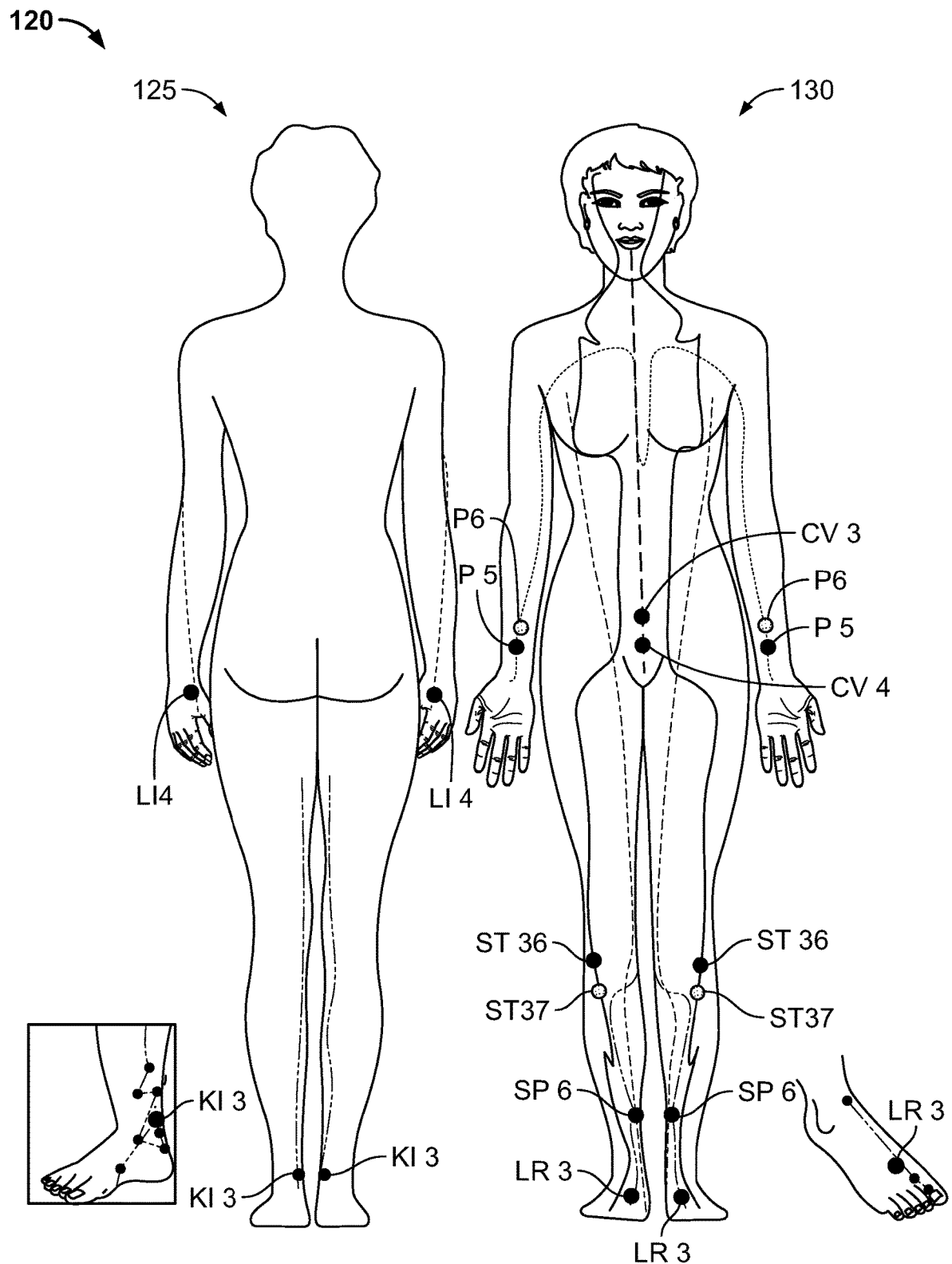
FIG. 1C is a diagram showing the locations of a plurality of specific acupuncture points used in the methods of treatment using electroacupuncture to treat hypertension, in accordance with embodiments of the present specification.

FIG. 1C is a diagram showing the locations of a plurality of specific acupuncture points that may be used in the methods of treatment using energy-stimulated acupuncture to treat hypertension, in accordance with embodiments of the present specification. As shown in FIG. 1C, the plurality of acupuncture points are located on posterior side 125 and anterior side 130 of a human body 120. The plurality of acupuncture points are identified as follows:

Jiangshi (P5) and Neiguan (P6) acupoints are located on the palmar side of the arm, 2 and 3 cm above the crease of the wrist, respectively, between the tendons of the long palmar and radial flexor muscles along the wrist, overlying the median nerve. It should be noted herein that the P6 acupoint alphanumeric corresponds to the pericardial 36 anatomy point.

Zusanli (St36) and Shangjuxu (St37) acupoints are located on the anterolateral side of the leg, 3 and 6 cm below the knee, respectively, and 1 cm lateral to the anterior crest of the tibia, overlying the deep peroneal nerve. It should be noted herein that the St36 acupoint alphanumeric corresponds to the stomach 36 specific anatomy point.

Hegu (LI4) acupoint is located on the radial flexor muscles along the wrist and radial side of the arm proximal to accessory carpel pad between abductor pollicis longus and tendon of brachioradialis, in the web between thumb and second finger, overlying the median nerve and the branches of the median nerve. It should be noted herein that the LI4 acupoint alphanumeric corresponds to the large intestine 4 specific anatomy point.

Sanyinjiao (Sp6) acupoint is located between the posterior margin of the tibia and the soleus muscle, 6 cm above the ankle, overlying the tibial nerve. It should be noted herein that the Sp6 acupoint alphanumeric corresponds to the spleen 6 specific anatomy point.

Zhongji (CV3) and Guanyuan (CV4) acupoints are located on the midline below the navel, 3/5 and 4/5 down from the navel to the superior edge of the pubic bone. It should be noted herein that the CV3 and CV4 acupoint alphanumerics correspond to the conception vessel 4 and conception vessel 4 specific anatomy points.

Taichong (LR3) acupoint is located on the dorsum of the foot in a depression distal to the junctions of the 1st and 2nd metatarsal bones, 5 cm above the web between the first and second toes, overlying branch of the deep peroneal nerve. It should be noted herein that the LR3 acupoint alphanumeric corresponds to the liver 3 specific anatomy point.

Taixi (KI3) acupoint is located at the midpoint between the medial malleolus of the ankle and the Achilles tendon, immediately posterior to the ankle, overlying the medial cutaneous branch of the saphenous nerve and tibial nerve. It should be noted herein that the KI3 acupoint alphanumeric corresponds to the kidney 3 specific anatomy point.

In some embodiments, each of the plurality of acupoints is stimulated concurrently throughout an entire stimulation session.

In some embodiments, each of the plurality of acupoints is stimulated at least partially, such as in subsets or groups, during the same stimulation session, however the stimulation may not be delivered concurrently, provided that each of the acupoints is stimulated, at some point, over the course of the stimulation session.

In some embodiments, either the plurality of acupoints are stimulated concurrently throughout the entire stimulation session or the plurality of acupoints are stimulated throughout the same stimulation session in subsets or groups, wherein said subsets or groups of the plurality of acupoints may be stimulated in series, in parallel or any other fashion until the entirety of the plurality of acupoints are stimulated during the same session.

Electro-Acupuncture Stimulation Parameters and Treatment Process

In various embodiments, a method of the present specification uses an electro-acupuncture device to deliver electrical stimulation therapy to a patient to treat hypertension. In some embodiments, the electro-acupuncture device may be configured as a TENS device.

However, in alternate embodiments, stimulation therapy may be delivered to the patient using a stimulator device, wherein the stimulation energy is laser or ultrasound.

In embodiments, the electro-acupuncture device is programmed using a plurality of stimulation parameters such as, but not limited to, the number of stimulation sessions per day or week, duration of the stimulation, time or moment of application of the stimulation sessions, intensity of stimulations, pulse shapes, pulse frequencies, pulse widths, pulse amplitude, pulse stimulation duty cycle, pulse stimulation continuity profile, or overall duration or course of stimulation treatment in days, weeks or months.

Figure 2:
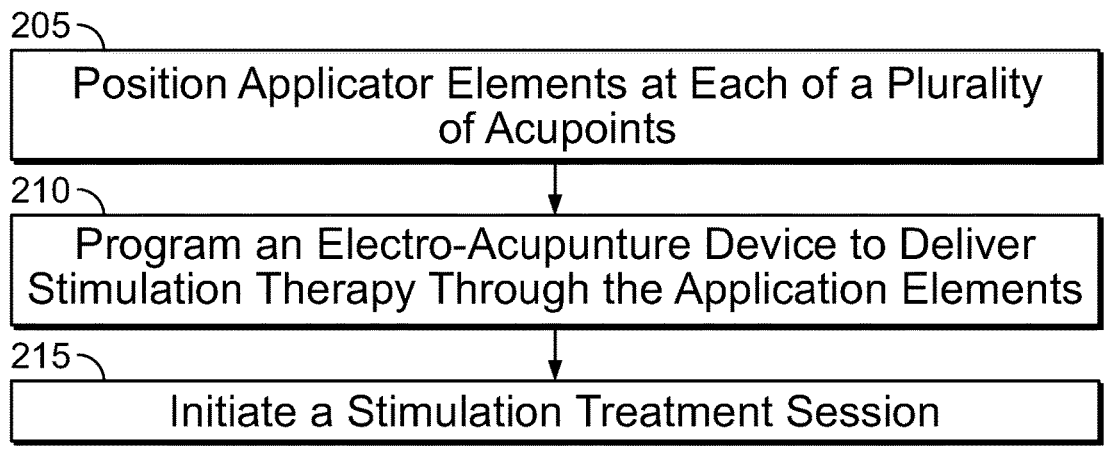
FIG. 2 is a flowchart depicting a method of using electroacupuncture to treat hypertension, in accordance with an embodiment of the present specification.

FIG. 2 is a flowchart of a plurality of steps of a method of using electro-acupuncture to treat hypertension, in accordance with an embodiment of the present specification. Referring now to FIGS. 1 and 2, at step 205 applicator elements are positioned on a patient, in an embodiment, at each of the following acupoints, as described with reference to FIG. 1: P6, LI4, St36, Sp6, CV3, CV4, LR3, and KI3. In alternate embodiments, the applicator elements are positioned at a subset of the aforementioned acupoints (P6, LI4, St36, Sp6, CV3, CV4, LR3, and KI3) at different times during the same stimulation session. In embodiments, the applicator elements comprise needles, electrodes, energy emitters such as lasers or ultrasound heads, and/or transcutaneous electrical stimulation electrodes, pads or contacts.

At step 210, an electro-acupuncture device is configured or programmed to deliver stimulation therapy to the patient through the positioned applicator elements. In embodiments, the stimulation therapy is delivered in accordance with the following exemplary stimulation parameters and ranges:

All needles, or applicator elements, are stimulated simultaneously.

Pulse Amplitude: 1 mA to 2 mA, 2 MA to 5 mA, up to paresthesia, between 0.5 mA and 8 mA and any whole number or fractional increment therein.

Pulse Frequency: 2 Hz to 5 Hz, 0.2 Hz to 10 Hz, less than 50 Hz, less than 100 Hz and any whole number or fractional increment therein.

Pulse Shape: Monophasic or Biphasic or any other pulse shape

All needles, or applicator elements, are stimulated to achieve bipolar stimulation.

At step 215, a stimulation treatment session is initiated. In one embodiment, the treatment session is preferably at least once per week for a duration of 30 minutes. In various embodiments, treatment sessions may range from once per two weeks to three times per week, where the time per session may range from 1 minute to 3 hours, less than 2 hours, from 5 minutes to 1 hour, 30 minutes, or any whole number or fractional increment therein.

In some embodiments, either the plurality of acupoints are stimulated concurrently throughout the entire stimulation session or the plurality of acupoints are stimulated throughout the same stimulation session in subsets or groups, wherein said subsets or groups of the plurality of acupoints may be stimulated in series, in parallel or any other fashion until the entirety of the plurality of acupoints are stimulated during the same session.

Case Study

Twenty women between the ages of 45 and 70 years old, presenting with hypertension, were randomly assigned (n=10) to either a first protocol comprising sympathoinhibitory electro-acupuncture (SEA) treatment at acupuncture points P5 and P6 and St36 and St37 or a second protocol comprising endocrine-sympathoinhibitory (ESEA) treatment at acupuncture points P6, LI4, St36, Sp6, CV3, CV4, LR3, and KI3. Both the first and second protocols are described in detail with reference to FIGS. 2 and 3, with the only distinction being the location and number of acupoints.

Figure 3:
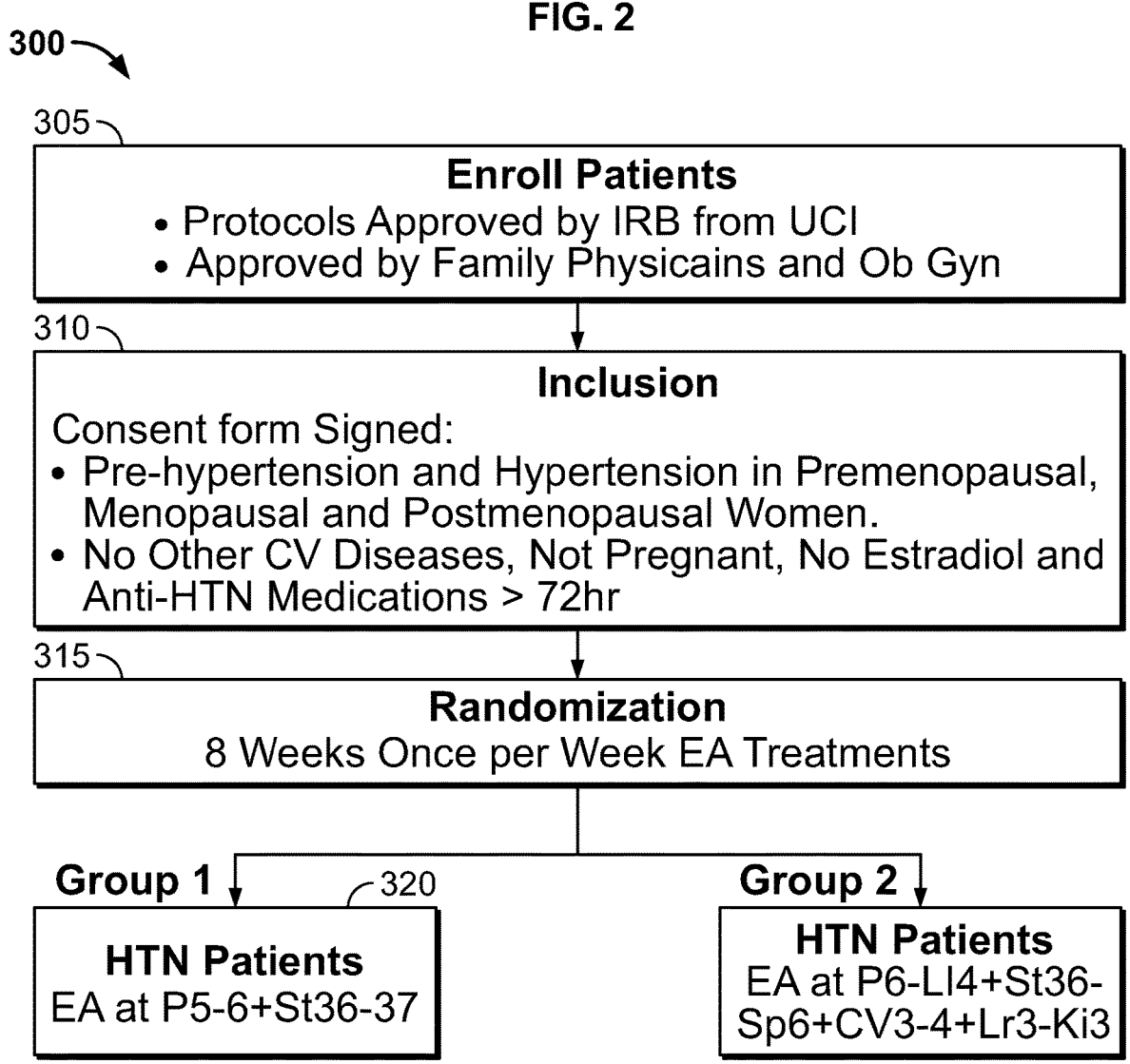
FIG. 3 is a flowchart depicting the steps of enrolling a patient and subjecting the patient to either a first protocol or a second protocol; and, FIG. 4 is an illustration showing a first set of systolic blood pressure (SBP) and diastolic blood pressure (DBP) graphs generated for hypertensive patients treated with endocrine-sympathoinhibitory EA (Electro-Acupuncture) and a second set of SBP and DBP graphs generated for the hypertensive patients treated with sympathoinhibitory EA.

Referring to FIG. 3, flowchart 300 depicts steps involved for enrolling a patient in the study of the present specification and subjecting the patient to either a first protocol or a second protocol. In step 305, the protocols were first subject to review by the facility, family physicians, and obstetricians/gynecologists. In step 310, a group of women were selected for inclusion in the study based on at least the following criteria:

The participants exhibited a pre-hypertension or hypertension condition and were pre-menopausal, menopausal, and post-menopausal women.

The participants did not have any other cardiovascular diseases and were not pregnant.

The participants were not on hormonal therapies (estradiol) and were not on antihypertensive medications.

The participants have an existing systolic blood pressure reading in a range of 130 mmHg to 200 mmHg.

It should be appreciated that men may be selected for inclusion using the same or similar criteria. In step 315, the participants were randomly placed (n=10) into a study using either a first protocol or a second protocol.

In step 320, the participants were subjected to either a first protocol comprising sympathoinhibitory electro-acupuncture (SEA) treatment at acupuncture points P5 and P6 and St36 and St37 or a second protocol comprising endocrine-sympathoinhibitory (ESEA) treatment at acupuncture points P6, LI4, St36, Sp6, CV3, CV4, LR3, and KI3. For each protocol, the participants were blinded to needle placement in acupoints. Needles were inserted and stimulated electrically once weekly using low current, low frequency (1-2 mA and 2-5 Hz), for 30 min, as described with respect to FIG. 2 above. Disposable sterile stainless steel needles were inserted bilaterally into sets of acupoints. Patients often described a paresthesia during stimulation of acupoints.

Laboratory Procedures

Blood samples were collected and placed on ice.

The blood samples were spun immediately and plasma was frozen until time of assay.

Norepinephrine was assayed in duplicate using an ELISA. The absorbance was measured spectrophotometrically at 450 nm using a microplate reader (Molecular Devices SpetraMax® Pro 384) with background correction at 600 nm.

Concentrations were determined with standard curve generated with regression curve fit using SoftMax Pro® (Molecular Devices) software.

Observations and Findings

Endocrine-sympathoinhibitory EA reduced systolic and diastolic blood pressures after the 8-week treatment protocol in middle-aged female patients with mild to moderate hypertension. However, an 8-week course of sympathoinhibitory EA (SEA) treatment did not decrease SBP, mean blood pressure (MBP), peak SBP and peak mean arterial pressure (MAP) in the 10 other subjects that were treated with the first protocol. The following observations and findings were documented after the enrolled women completed an 8-week course of treatment.

The blood pressure lowering responsiveness (≥−6 mmHg) to the second protocol comprising endocrine-sympathoinhibitory EA (ESEA) was 80% while only 33% of the subjects treated with the first protocol comprising sympathoinhibitory EA (SEA) lowered their blood pressures. Peak systolic blood pressure (SBP) during 24 hours dropped from 168±5.1 to 156±3.3 mmHg (P=0.003) while averaged 24 hour SBP dropped from 136±3.8 to 128±2.5 mmHg (P=0.021) in 10 subjects treated with endocrine-sympathoinhibitory EA (ESEA). In addition, the averaged 24 hour mean blood pressure (MBP) and peak MBP decreased respectively with p-values of 0.035 and 0.012 in the 10 subjects treated with endocrine-sympathoinhibitory EA (ESEA).

Figure 4:
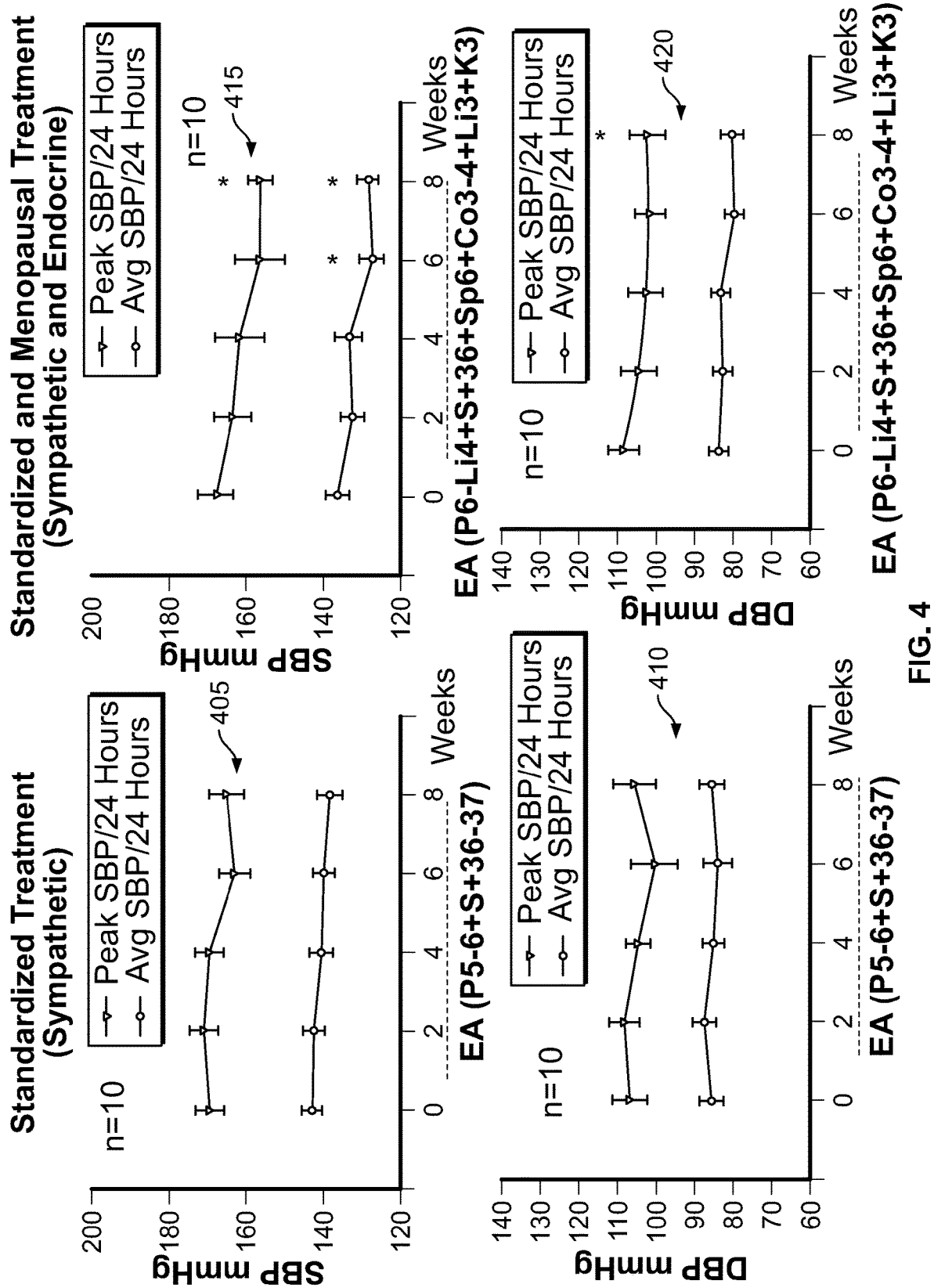

FIG. 4 shows a first set of systolic blood pressure (SBP) and diastolic blood pressure (DBP) graphs 405, 410 generated for the hypertensive patients treated with the first protocol EA at acupoints P5-6+St36-37 while a second set of SBP and DBP graphs 415, 420 generated for the hypertensive patients treated with the second protocol EA at acupoints P6, LI4, St36, Sp6, CV3, CV4, LR3, and KI3. As can be observed from the graphs 415, 420, SBP and DBP averaged over 24 hour were reduced for 8 weeks in 8 middle-aged hypertensive women treated with the second protocol. On the other hand, graphs 405, 410 show that peak SBP and DBP tended to decrease at week 6 but not after week 8 in the group of women treated with the second protocol.

Plasma norepinephrine was reduced in patients with reduced blood pressure after the ESEA treatment. Specifically, plasma norepinephrine reduced in 9 patients from 381±123 pg/ml to 186±69 pg/ml (P=0.008) with decreased blood pressure after the 8-week ESEA treatment. Reduced norepinephrine is indicative of decreased sympathetic tone leading to a decrease in blood pressure. This study indicates that EA decreases sympathoexcitatory neuronal activity and cardiovascular responses. Decreases in both blood pressure and norepinephrine confirm the action of EA-inhibition on sympathetic tone. Thus, endocrine-sympathoinhibition EA in middle-aged hypertensive women enhances blood pressure lowering responsiveness compared with sympathoinhibitory EA treatment.

Accordingly, in one embodiment, the energy stimulated acupuncture processes disclosed herein, particularly with respect to patients having a systolic blood pressure reading in a range of 130 mmHg to 200 mmHg and particularly with respect to the use of electroacupuncture, will result in a minimum of a 2 mmHg to 12 mmHg decrease in systolic blood pressure (preferably 4 to 8 mmHg and more preferably 6 mmHg) over a four week period, preferably a six week period, presuming at least one treatment session, as described above, per week.

Accordingly, in one embodiment, the energy stimulated acupuncture processes disclosed herein, particularly with respect to patients having a systolic blood pressure reading in a range of 130 mmHg to 200 mmHg and particularly with respect to the use of electroacupuncture, will result in a minimum 10% reduction (preferably 10% to 50%, and more preferably 20%) of a patient's plasma norepinephrine levels, relative to pre-treatment, after a four week treatment period, preferably a six week treatment period, presuming at least one treatment session, as described above, per week.

The above examples are merely illustrative of the many applications of the system of present specification. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

We claim:

1. A transcutaneous electrical stimulation device adapted to treat hypertension in a patient comprising:
   a stimulator configured to generate electrical energy;
   electrodes in electrical communication with the stimulator device;
   needles coupled to the electrodes and adapted to be positioned in physical contact with each of a plurality of acupoints, wherein the plurality of acupoints consists of P6, LI4, St36, Sp6, CV3, CV4, LR3, and KI3.

2. The transcutaneous electrical stimulation device of claim 1, wherein the electrical energy is defined by a pulse amplitude in a range of 0.5 mA to 8 mA.

3. The transcutaneous electrical stimulation device of claim 2, wherein the pulse amplitude is in a range of 1 mA to 2 mA.

4. The transcutaneous electrical stimulation device of claim 1, wherein the electrical energy is defined by a pulse frequency in a range of 0.2 Hz to 10 Hz.

5. The transcutaneous electrical stimulation device of claim 4, wherein the pulse frequency is in a range of 2 Hz to 5 Hz.

6. The transcutaneous electrical stimulation device of claim 1, wherein the stimulator is configured to generate the electrical energy for a stimulation session and wherein the stimulation session is defined by a time period in a range of one minute to three hours.

7. The transcutaneous electrical stimulation device of claim 6, wherein the stimulation session is applied at least once per week.

8. The transcutaneous electrical stimulation device of claim 6, wherein the stimulation session is applied no more than five times per week.

9. The transcutaneous electrical stimulation device of claim 1, wherein the stimulator is configured to generate the electrical energy for a stimulation session and wherein, in the stimulation session, the electrical energy is applied to each of the needles concurrently.

10. The transcutaneous electrical stimulation device of claim 1, wherein the stimulator is configured to generate the electrical energy for a stimulation session and wherein, in the stimulation session, the electrical energy is not applied to each of the needles concurrently.

11. A laser stimulation device adapted to treat hypertension in a patient comprising:
a stimulator configured to generate light energy;
light energy applicators in electrical communication with the stimulator device, wherein the light energy applicators are adapted to be positioned in physical contact with each of a plurality of acupoints, wherein the plurality of acupoints consists of P6, LI4, St36, Sp6, CV3, CV4, LR3, and KI3.

12. The laser stimulation device of claim 11, wherein the stimulator is configured to generate light energy having a wavelength in a range of 700 to 1000 nm.

13. The laser stimulation device of claim 11, wherein the stimulator is configured to generate light energy having a power level in a range of 100 to 400 mW.

14. The laser stimulation device of claim 11, wherein the stimulator is configured to generate light energy having a power density of 0.3 W/cm$^2$ to 0.5 W/cm$^2$.

15. The laser stimulation device of claim 11, wherein the light energy applicators are adapted to apply a spot size in a range of 0.2 cm$^2$ to 0.6 cm$^2$.

16. The laser stimulation device of claim 11, wherein the stimulator is configured to generate light energy for a treatment time and wherein the treatment time is in a range of 5 seconds to 240 seconds for each of the plurality of acupoints.

17. The laser stimulation device of claim 11, wherein the stimulator is configured to generate light energy for a treatment session and wherein the stimulator is configured to generate light energy having an energy dose per session in a range of 0.2 Joules to 0.7 Joules.

* * * * *